United States Patent [19]

Hepford

[11] Patent Number: 5,776,306

[45] Date of Patent: Jul. 7, 1998

[54] RECREPED ABSORBENT PAPER PRODUCT AND METHOD FOR MAKING

[75] Inventor: Richard R. Hepford, Folcroft, Pa.

[73] Assignee: Kimberly-Clark Worldwide, Inc., Neenah, Wis.

[21] Appl. No.: 484,591

[22] Filed: Jun. 7, 1995

[51] Int. Cl.$^6$ .................. B31F 1/12; D21F 11/00
[52] U.S. Cl. .................. 162/112; 162/134; 162/135; 264/128; 264/136; 264/283; 156/291
[58] Field of Search .................. 162/111, 112, 162/134, 135; 156/291; 264/128, 136, 283

[56] References Cited

U.S. PATENT DOCUMENTS

| | | |
|---|---|---|
| 1,294,794 | 2/1919 | Gretsch . |
| 3,879,257 | 4/1975 | Gentile et al. .................. 162/112 |
| 3,903,324 | 9/1975 | Gukelberger, Jr. et al. .................. 427/88 |
| 4,000,237 | 12/1976 | Roberts, Jr. .................. 264/128 |
| 4,208,459 | 6/1980 | Becker et al. .................. 428/154 |
| 4,326,000 | 4/1982 | Roberts, Jr. .................. 428/153 |
| 4,507,173 | 3/1985 | Klowak et al. .................. 162/112 |
| 4,610,743 | 9/1986 | Salmeen et al. .................. 156/183 |
| 4,978,565 | 12/1990 | Pigneul et al. .................. 428/156 |

FOREIGN PATENT DOCUMENTS

| | | | |
|---|---|---|---|
| 2177856 | 11/1973 | France .................. | D21F 11/00 |
| 2227369 | 11/1974 | France .................. | D04H 1/00 |
| 94/23128 | 10/1994 | WIPO .................. | D21H 27/02 |

*Primary Examiner*—Stanley S. Silverman
*Assistant Examiner*—Jose A. Fortuna
*Attorney, Agent, or Firm*—Gregory E. Croft

[57] ABSTRACT

A method of making a bonded and creped type absorbent paper web that has improved bulk to peel strength characteristics includes steps of (a) printing a low density pattern of a bonding material onto a first and a second side of a paper web; and (b) in no particular sequence with respect to step (a), printing a high density pattern of a bonding material onto the first side of the paper web. Steps (a) and (b) are performed so that the high density pattern of bonding material penetrates into the paper web by a distance that is about 166 to about 470 percent of the distance by which the low density pattern of bonding material penetrates into the web. This results in a web that has superior bulk and peel strength characteristics. Another characteristic of the product is that it has a visible depression pattern in one surface, but not the other surface, which creates an attractive aesthetic effect and has functional benefits as well.

24 Claims, 4 Drawing Sheets

RECREPED ABSORBENT PAPER PRODUCT AND METHOD FOR MAKING

FIELD OF THE INVENTION

This invention relates to an improved recreped-type absorbent fibrous web material that is made from papermaking fibers for use as sanitary disposable towels and wipers, and to a method for making such material.

DESCRIPTION OF THE PRIOR ART

Companies such as Scott Paper Company, the assignee hereof, continue to develop disposable absorbent paper substitutes for conventional cloth products such as wipers, tissues and towels.

To successfully gain consumer acceptance, such products must closely simulate cloth in both consumer perception and in performance. Accordingly, certain physical properties must be present in a successful product, including softness, strength, stretchability, absorbency, ability to wipe dry, bulk and abrasion resistance. Depending upon the intended use of the product, some properties are more desirable than others. Softness is highly desirable for almost all absorbent paper products, regardless of intended use. This is true not only because consumers find it more pleasant to handle soft products, but also because softness enables the product to readily conform to the shape that is dictated by job requirements. Strength and the ability to stretch are two other desirable properties, particularly in products that are to be used for heavy duty applications. Also, it is desirable for a product to have good abrasion resistance if it is to be used for wiping, cleaning or scouring. For products that are designed for use as a facial tissue, poor abrasion resistance can result in pilling or dusting of fibers from the product when being handled by the consumer. Bulk is important not only because it enables the paper product to feel like cloth, but also because it is favorably interrelated to other desirable properties, such as softness and absorbency.

Some properties tend to be inversely related, meaning that an increase in one property is usually accompanied by a decrease in another property. For example, an increase in web density or fiber concentration (the closeness of the fibers to each other) increases the ability of the web to wipe dry or pick up moisture, due to the greater capillary action of the small spaces between the fibers. However, an increase in closeness of the fibers decreases the space between the fibers that is available for holding the moisture, and thus reduces the absorbency, in terms of quantity, of the web. Perhaps an even more demonstrative example of the adverse interrelation between properties is represented by the relationship between strength and softness. It has generally been believed that conventional methods employed to produce soft paper necessarily result in strength reduction. This is because conventional paper products are formed from aqueous slurries, and their principal source of strength is the interfiber bonds that are formed by the hydrate bonding process associated with papermaking. Paper that has a heavy concentration of such papermaking bonds is usually stiff. To soften the paper, it is necessary to reduce the stiff bonds, an action that also results in a loss of strength. The method most commonly employed to reduce the stiff papermaking bonds is to crepe the paper from a drying surface with a doctor blade, disrupting and breaking many of the interfiber bonds in the paper web. Other methods that have been used to reduce the bonds contrast with creping by preventing formation of the bonds, rather than breaking them after they are formed. Examples of these other methods are chemical treatment of the papermaking fibers to reduce their interfiber bonding capacity before they are deposited on the web-forming surface, use of unrefined fibers in the slurry, inclusion into the slurry of synthetic fibers not exhibiting the ability to form papermaking bonds, and use of little or no pressing of the web to remove the water from the paper web after it is deposited on the web forming surface. This latter method reduces formation of bonds by reducing close contact of the fibers with each other during the forming process. All of these methods can be employed successfully to increase the softness of paper webs, but only with an accompanying loss of strength in the web.

Attempts to restore the strength lost by reducing the papermaking bonds have included adding to the web bonding materials that are capable of adding strength to a greater degree than adding stiffness to the web. One method that has been used to apply bonding materials to the web is to add the bonding material to the aqueous slurry of fibers and deposit it on the web-forming surface along with the fibers. With this method, the bonding material can be distributed evenly throughout the web, avoiding the harshness that would accompany concentrations of bonding material. However, this method reduces the absorbency of the web because it fills the pores between the fibers with bonding material. It also bonds the web uniformly throughout, the disadvantages of which will be explained subsequently.

Another method that has been used to apply bonding material to the web is to apply the bonding material in a spaced-apart pattern to the web. With this method, the majority of the web surface does not contain absorbency-reducing bonding material. Webs made entirely or principally from papermaking fibers require bonding areas to be quite close together because papermaking fibers are very short, generally less than one-quarter of an inch long. Initially it was thought that to apply sufficient bonding material in a pattern to a paper web to the degree necessary to bond each fiber into the network would result in a harsh sheet, having poor softness characteristics, particularly in the areas where the bonding material is located. However, U.K. Pat. No. 1,294,794 disclosed a method that mitigated such harshness which, in its preferred form, consisted of first forming a fibrous web under conditions that result in very low interfiber bonding strength. Strength is then imparted to the web by applying bonding material to one surface of the web in a fine spaced-apart pattern. The harshness in the bonded areas is reduced by tightly adhering bonded portions of the web to a creping surface and removing with a doctor blade, thus finely creping the bonded portions to soften them. This form of controlled creping also results in a number of other property improvements. For example, selective creping of the bonded areas in the surface of the web creates contraction of the surface of the web in all directions, resulting in an increase in stretch in both the machine direction and the cross-machine direction of the web. Also, the portions of the web where the bonding material is not located are generally disrupted by the creping action, resulting in an increase in bulk of the web, an increase in the softness of the web, and an increase in absorbency. At certain locations within the web, close to the bonding material, the web develops internal split portions which further enhance the absorbency, softness, and bulk of the web. It is this effect on the portions where the bonding material is not located which does not exist, at least to the same extent, in the web formed by addition of bonding material to the aqueous slurry of fibers. This method produces a paper web with outstanding softness and strength, two properties which were previously believed to be almost mutually exclusive. It also produces a web with excellent absorbency properties due to the bonding material being confined to only a minor portion of the web surface. Furthermore, the compaction of the surface fibers due to the shrinkage of the bonded portions on the web creates one surface of the web which has improved wipe-dry characteristics. It is also believed that pressing the web to a creping surface while the web has moist portions in the surface region due to the uncured or undried bonding material causes the fibers in those moist areas to compact. This method is particularly useful in production of webs in a lower basis weight range for such use as bathroom tissues.

Unfortunately, the method disclosed in the UK '794 patent had shortcomings in making webs for heavier duty use such as for towels and facial tissues where greater strength, bulk and absorbency is desired. Examples of such shortcomings are poor abrasion resistance (or excessive pilling and dusting) and inability to hold to the web the fibers on the nonbonded side of the web, as well as less strength in the overall web than may be desired. These properties could be improved by causing the bonding material to penetrate completely through the web to create a network of bonding material which passes entirely through the web, but the web would benefit less from the improvements afforded by the UK '794 invention. Bonding the web with the bonding material extending completely through the web would greatly reduce the disruption of the fibers within the web upon creping, and therefore, result in a reduction of bulk, softness, and absorbency. Also, complete penetration of the bonding material through the web is difficult to accomplish on heavier basis weight webs and attempts to do so result in concentrations of excess bonding material at the web surface where much of it is ineffective for strengthening interfiber bonds. Furthermore, if complete penetration of the bonding material does result, the bonding material in the interior of the web will not be as efficiently used to increase abrasion resistance of the web as when it is placed only in the surface of the web. Placement of the bonding material in the interior of the web is not only an inefficient use of the expensive bonding material, but results in harsher feel to the web due to the inability of the creping action to soften the bonded portions as effectively. Also, one desirable feature of the '794 invention that would be reduced by bonding completely through the web is the ability to create a web surface of compacted fibers having good wipe-dry characteristics while at the same time creating a bulky web capable of absorbing a large amount of moisture. These properties are only of minor importance when producing a product for such uses as bathroom tissues, but where the product is to be used for wipers, facial tissue or towels, it is very important. This shortcoming detracts from the '794 invention as a method of producing a wiper, facial tissue or towel product.

An improvement over the UK '794 invention described in U.S. Pat. No. 4,326,000 to Roberts involves a laminate-like first surface region that has surface bonding material disposed within it, preferably in a fine, spaced-apart pattern, to bond the fibers into a strong network within the surface region and to impart abrasion-resistance to that side of the web. Penetrating bonding material is disposed within the central core region in a fine, spaced-apart pattern which occupies less area in the plane of the web than the surface bonding material does in the first surface region. The penetrating bonding material in the central core region extends entirely through the central core region and connects the two surface regions together. To interconnect the two surface regions, the penetrating bonding material extends through the central core region to within at least one fiber thickness of the web surface opposite the laminate-like first surface region where it not only interconnects the two surface regions, but also increases abrasion-resistance to the second, opposite surface. The second surface region has no pattern of surface bonding material apart from the penetrating bonding material and is no more than the outer surface of the central core region, in which case the web has only two planar regions. In terms of appearance, the pattern of penetrating bonding material is visible on both sides of the creped product.

Although the Roberts process represents a significant improvement in terms of product property optimization, there is an inverse relationship between bulk generation and peel (z-direction) tensile strength, meaning that as product bulk increases, peel strength lessens, sometimes to the point where total delamination of the sheet occurs. A need exists in this area of technology for a process that allows for high bulk generation without sacrificing peel strength. In addition, the industry is constantly striving for products that have improved aesthetic characteristics, so improvements in this area would be well received as well.

SUMMARY OF THE INVENTION

Accordingly, it is an object of the invention to provide a process of the general type described above that allows for high bulk generation without sacrificing peel strength. It is further an object of the invention to provide a product that has superior aesthetic characteristics.

In order to achieve the above and other objects of the invention, a method of making a bonded and creped type absorbent paper web that has improved bulk to peel strength characteristics includes steps of (a) printing a low density pattern of a bonding material onto a first and a second side of a paper web; (b) in no particular sequence with respect to step (a), printing a high density pattern of a bonding material onto the first side of the paper web, steps (a) and (b) being performed so that the high density pattern of bonding material penetrates into the paper web by a distance that is about 167 to about 470 percent of the distance by which the low density pattern of bonding material penetrates into the web; and (c) creping the paper web to a degree that is sufficient to impart a significant degree of bulk to areas of the paper web that have the low density pattern of bonding material printed thereon, but not the areas of the paper web that have the high density pattern printed thereon, whereby both superior bulk and peel strength characteristics are imparted to the absorbent web product.

A method of making a bonded and creped type absorbent paper web that has improved bulk to peel strength characteristics, includes, according to a second aspect of the invention, steps of (a) printing a low density pattern of a bonding material onto a first and a second side of a paper web with a first gravure roll that has a depth of about 30 microns to about 100 microns; (b) in no particular sequence with respect to step (a), printing a high density pattern of a bonding material onto the first side of the paper web with a second gravure roll that has a depth of about 55 microns to about 125 microns; and (c) creping the paper web to a degree that is sufficient to impart a significant degree of bulk to areas of the paper web that have the low density pattern of bonding material printed thereon, but not the areas of the paper web that have the high density pattern printed thereon, whereby both superior bulk and peel strength characteristics are imparted to the absorbent web product.

An improved single ply absorbent web product includes, according to a third aspect of the invention, a bulky absorbent web comprising predominately papermaking fibers, the bulky web having a first surface and a second, opposite surface; and a pattern, the pattern including at least one depression that is defined in the first surface, but not in the second surface, whereby a single ply absorbent web product is provided that has a pattern defined on one side of the web, but not the other side.

These and various other advantages and features of novelty which characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there is illustrated and described a preferred embodiment of the invention.

DETAILED DESCRIPTION OF THE PREFERRED EMBODIMENT(S)

Figure 1:
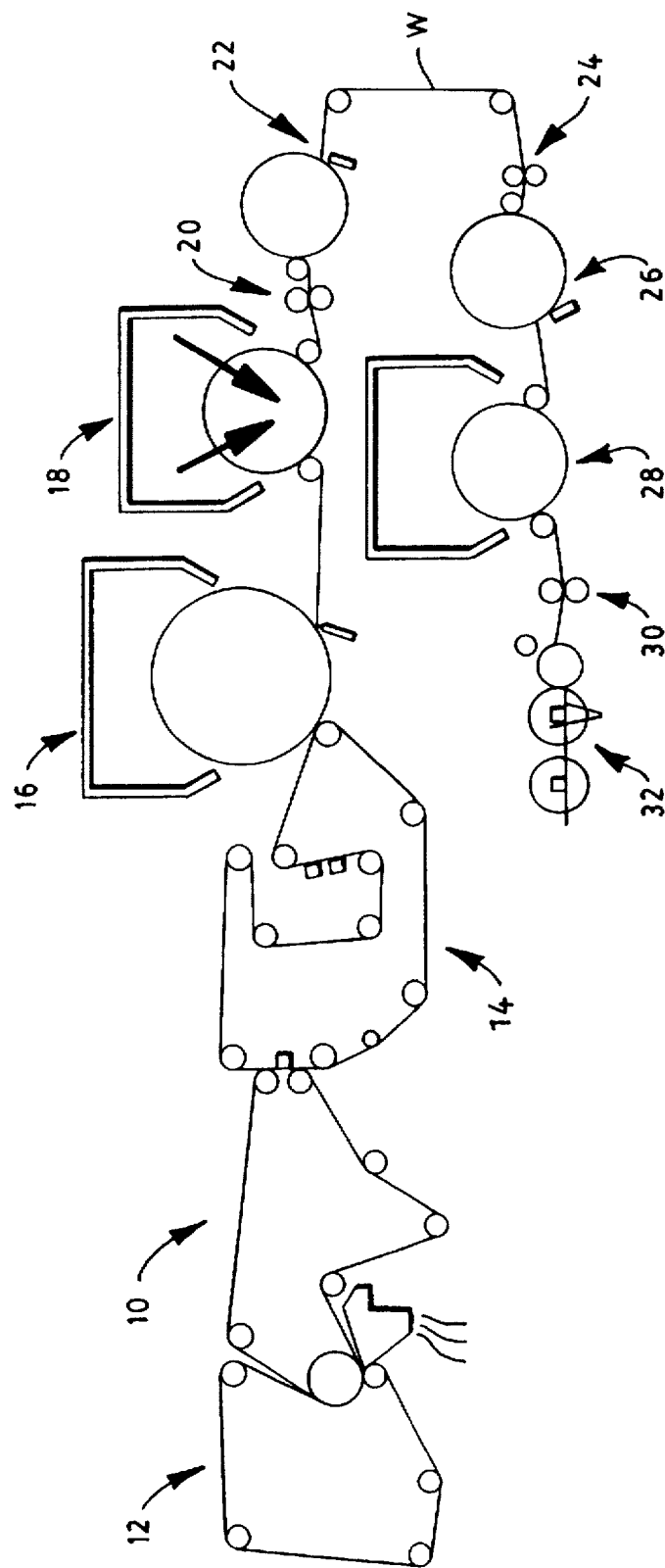
FIG. 1 is a schematic depiction of an improved system for making a bonded and creped type absorbent paper web that is constructed according to a preferred embodiment of the invention.

Referring now to the drawings, wherein like reference numerals designate corresponding structure throughout the views, and referring in particular to FIG. 1, an improved to system 10 for making a bonded and creped type absorbent paper web preferably includes, as is common in such systems, a twin wire former 12, a press section 14, a Yankee dryer 16, a transpiration dryer 18 and a recreping section that includes a first printer 20, a first crepe dryer 22, a second printer 24 and a second crepe dryer 26. System 10 further includes a cure dryer 28, a cool roller pair 30 and a reel 32 for winding the finished absorbent paper product into a roll.

Aside from the novel aspects of the invention, which are discussed below, the elements of system 10 referred to above operate together in the conventional manner, which is well known to those having skill in this area of technology.

Figure 2:
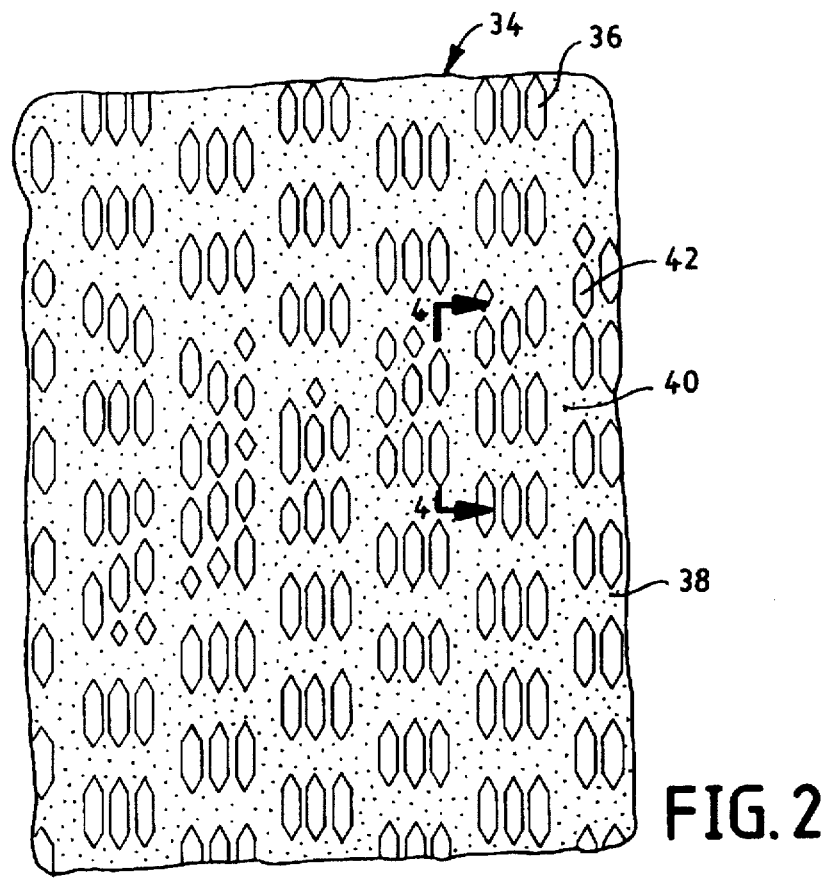
FIG. 2 is a fragmentary surface view of a first gravure roll in the system depicted in FIG. 1.
Figure 4:
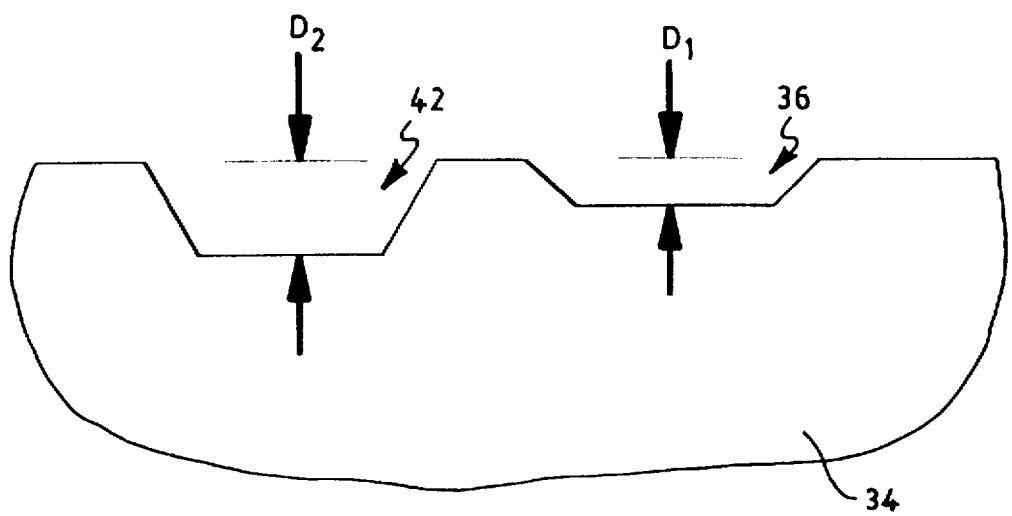
FIG. 4 is a fragmentary cross sectional view taken along lines 4—4 in FIG. 2.

Referring now to FIGS. 2 and 4, it will be seen that first printer 20 includes a first gravure roll 34 that has a relatively low density background pattern 38 defined therein a regularly spaced pattern of canoe shaped depressions 36. Superimposed upon the background pattern 38 is a densified pattern 40 of canoe shaped depressions 42 that have a significantly greater depth and volumetric capacity than the canoe shaped depressions 36 of the background pattern 38 do. Referring to FIG. 4, it will be seen that the depressions 36 of the background pattern have a depth $D_1$ and that the depressions 42 of the densified pattern 40 have a depth $D_2$. $D_2$ is preferably about 140 to about 200 percent of depth $D_1$. This corresponds to a degree of penetration of the bonding material into the web W that is applied by gravure roll 34 for the densified pattern 40 that is about 166 to about 470 percent of the degree of penetration that takes place for the background pattern 38. Preferably, the depressions 36 of the background pattern will cause bonding material to penetrate about 15 to 30 percent into the thickness of the web, while the depressions 42 will cause penetration of about 50 to 70 percent into the web.

Figure 3:
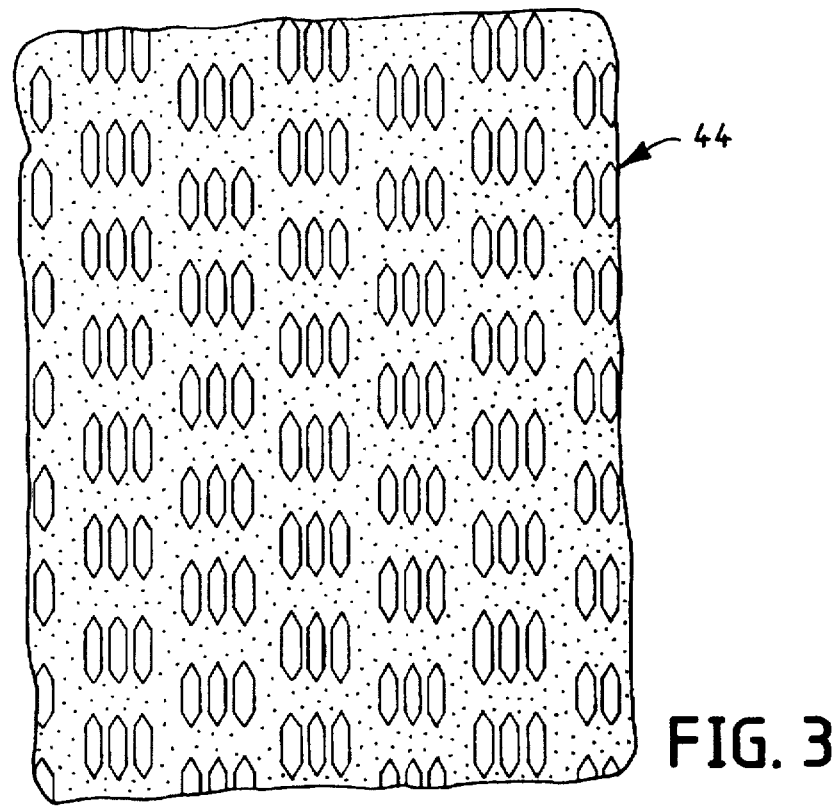
FIG. 3 is a fragmentary surface view of a second gravure roll in the system that is shown in FIGS. 1 and 2.

FIG. 3 is a fragmentary top surface view of a second gravure roller 44, which is part of the second printer station 24 shown in FIG. 1. Second gravure roller 44 has only the background pattern 38 defined therein, which is preferably identical to the background pattern 38 that is depicted in FIGS. 2 and 4.

Preferably, the low density background pattern 38 is printed onto from about 30 percent to about 50 percent of the total surface of both the first side of the web, by the first gravure roller 34, and of the second side of the web, by the second gravure roller 44. Most preferably, background pattern 38 is printed onto about 40 percent of the total surface of both the first and second sides of the web.

The high density pattern 40 is preferably printed onto from between about 5 percent to about 15 percent of the total surface of the first side of the web by the first gravure roller 34. Most preferably, the high density pattern 40 is printed onto about 8 percent of the total surface of the first side of the web.

Preferably, depth $D_1$ of the background pattern 38 is from between about 30 to about 100 microns, with a most preferred depth of about 60 microns. Depth $D_2$ is preferably between 55 microns to about 125 microns, with a most preferred depth of about around 90 microns.

In operation, an absorbent web W is formed by the twin wire former 12 and is dried by the press section 14, the Yankee dryer 16 and the transpiration dryer 18 in a manner that is well known in this area of technology. The web W is than passed through the first printer station 20, where a bonding material, preferably a latex, is printed onto a first side of the web by the first gravure roll 34. The pattern that is printed onto the first side of the web by the first gravure roll 34 will include the background pattern 38 discussed above and the densified pattern 40 that is also discussed in detail above. The printed web W is then passed through the crepe dryer 22 and is creped to break interfiber bonds and increase bulk as is well known in the industry. The web W is then passed to the second printer 24, where a second, opposite side of the web W is printed by the second gravure roll 44 with the background pattern 38. The web is then passed through the second crepe dryer 26, adding additional bulk to the web. The web is then passed through the cure dryer 28, through a pair of cool rolls 30 and onto the reels 32 for winding.

Figure 5:
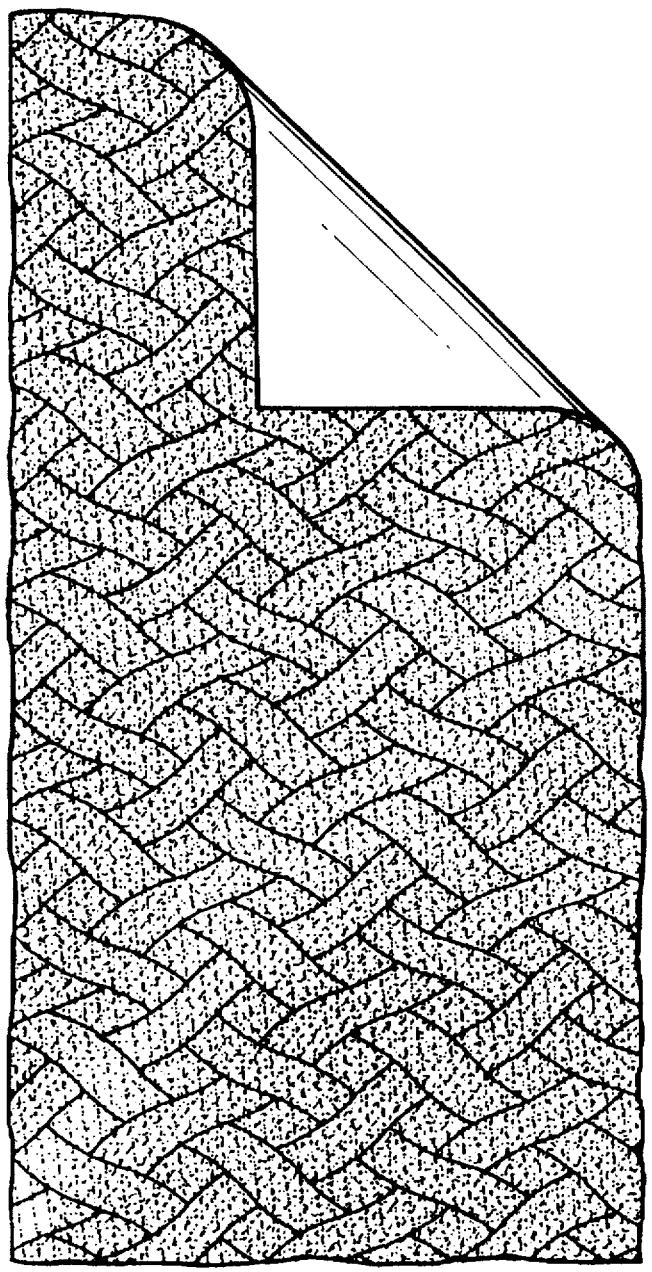
FIG. 5 is a drawing showing the surface texture of the first and second sides of a completed web product according to the invention.

According to one novel aspect of the invention, and as is shown in FIG. 5, it has been found that by printing the bonding material in the densified and background patterns as specified above, that a visible pattern that corresponds to the densified pattern 40 printed by the first gravure roll 34 will appear as depressions on the first side of the web after the web exits the second crepe dryer 26, and that no pattern at all will be visible on the second side of the web. Accordingly, the process described herein results in a single ply absorbent web product that has a pattern defined on one side of the web, but not the other side. In additional to the obvious ascetic advantageous to the product, functional benefits are achieved as well, such as resistance to nesting during winding.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. A method of making a bonded and creped type absorbent paper web that has improved bulk to peel strength characteristics, comprising steps of:
   (a) printing a low density pattern of a bonding material onto a first and a second side of a paper web with a gravure roll that has a pattern defined thereon to a depth that is from between about 30 to about 100 microns;
   (b) in no particular sequence with respect to step (a), printing a high density pattern of a bonding material onto the first side of the paper web, steps (a) and (b) being performed so that the high density pattern of bonding material penetrates into the paper web by a distance that is about 166 to about 470 percent of the distance by which the low density pattern of bonding material penetrates into the web, said high density pattern being visible only on the first side of the web; and
   (c) creping the paper web to a degree that is sufficient to impart a significant degree of bulk to areas of the paper web that have the low density pattern of bonding material printed thereon, but not the areas of the paper web that have the high density pattern printed thereon, whereby both superior bulk and peel strength characteristics are imparted to the absorbent web product.

2. A method according to claim 1, wherein step (a) is performed so that the low density pattern is printed onto from between about 30 percent to about 50 percent of the total surface of both the first and the second side of the web.

3. A method according to claim 2, wherein step (a) is performed so that the low density pattern is printed onto about 40 percent of the total surface of both the first and the second side of the web.

4. A method according to claim 1, wherein step (b) is performed so that the high density pattern is printed onto from between about 5 percent to about 15 percent of the total surface of the first side of the web.

5. A method according to claim 4, wherein step (b) is performed so that the high density pattern is printed onto about 8 percent of the total surface of the side of the web.

6. A method according to claim 1, wherein step (a) is performed with a gravure roll that has a pattern defined thereon to a depth that is about 60 microns.

7. A method according to claim 1, wherein step (b) is performed with a gravure roll that has a pattern defined thereon to a depth that is between about 55 microns to about 125 microns.

8. A method according to claim 7, wherein step (b) is performed with a gravure roll that has a pattern defined thereon to a depth that is about 90 microns.

9. A method according to claim 1, wherein step (c) comprises creping the web twice for additional bulk.

10. A method of making a bonded and creped type absorbent paper web that has improved bulk to peel strength characteristics, comprising steps of:
    (a) printing a low density pattern of a bonding material onto a first and a second side of a paper web with a first gravure roll that has a pattern defined thereon at a depth of about 30 microns to about 100 microns;
    (b) in no particular sequence with respect to step (a), printing a high density pattern of a bonding material onto the first side of the paper web with a second gravure roll that has a pattern defined thereon to a depth that is about 55 microns to about 125 microns wherein the high density pattern is visible only on the first side of the web; and
    (c) creping the paper web to a degree that is sufficient to impart a significant degree of bulk to areas of the paper web that have the low density pattern of bonding material printed thereon, but not the areas of the paper web that have the high density pattern printed thereon, whereby both superior bulk and peel strength characteristics are imparted to the absorbent web product.

11. A method according to claim 10, wherein step (a) is performed so that the low density pattern is printed onto from between about 30 percent to about 50 percent of the total surface of both the first and the second side of the web.

12. A method according to claim 11, wherein step (a) is performed so that the low density pattern is printed onto about 40 percent of the total surface of both the first and the second side of the web.

13. A method according to claim 10, wherein step (b) is performed so that the high density pattern is printed onto from between about 5 percent to about 15 percent of the total surface of the first side of the web.

14. A method according to claim 13, wherein step (b) is performed so that the high density pattern is printed onto about 8 percent of the total surface of the side of the web.

15. A method according to claim 10, wherein step (c) comprises creping the web twice for additional bulk.

16. A method of making a bonded and creped type absorbent paper web that has improved bulk to peel strength characteristics, comprising steps of:
    (a) printing a low density pattern of a bonding material onto a first and a second side of a paper web with a gravure roll that has a pattern defined thereon to a depth that is from between about 30 to about 100 microns;
    (b) in no particular sequence with respect to step (a), printing a high density curvilinear pattern of a bonding material onto the first side of the paper web, steps (a) and (b) being performed so that the high density pattern of bonding material penetrates into the paper web by a distance that is about 166 to about 470 percent of the distance by which the low density pattern of bonding material penetrates into the web; and
    (c) creping the paper web to a degree that is sufficient to impart a significant degree of bulk to areas of the paper web that have the low density pattern of bonding material printed thereon, but not the areas of the paper web that have the high density pattern printed thereon, whereby both superior bulk and peel strength characteristics are imparted to the absorbent web product.

17. A method according to claim 16, wherein step (a) is performed so that the low density pattern is printed onto from between about 30 percent to about 50 percent of the total surface of both the first and the second side of the web.

18. A method according to claim 17, wherein step (a) is performed so that the low density pattern is printed onto about 40 percent of the total surface of both the first and the second side of the web.

19. A method according to claim 16, wherein step (b) is performed so that the high density pattern is printed onto from between about 5 percent to about 15 percent of the total surface of the first side of the web.

20. A method according to claim 19, wherein step (a) is performed so that the high density pattern is printed onto about 8 percent of the total surface of the side of the web.

21. A method according to claim 16, wherein step (a) is performed with a gravure roll that has a pattern defined thereon to a depth that is about 60 microns.

22. A method according to claim 16, wherein step (b) is performed with a gravure roll that has a pattern defined thereon to a depth that is between about 55 microns to about 125 microns.

23. A method according to claim 22, wherein step (b) is performed with a gravure roll that has a pattern defined thereon to a depth that is about 90 microns.

24. A method according to claim 16, wherein step (c) comprises creping the web twice for additional bulk.

* * * * *